United States Patent [19]
Den Otter et al.

[11] 3,994,892
[45] Nov. 30, 1976

[54] PROCESS FOR PURIFYING CYANURIC ACID

[75] Inventors: Marinus J. A. M. Den Otter, Munstergeleen; Augustinus P. H. Schouteten, Maastricht; Lambertus P. G. Hawinkels, Montfort, all of Netherlands

[73] Assignee: Stamicarbon B.V., Geleen, Netherlands

[22] Filed: Oct. 29, 1975

[21] Appl. No.: 627,003

[30] Foreign Application Priority Data
Nov. 12, 1974 Netherlands ................... 7414704

[52] U.S. Cl. ............................................. 260/248 A
[51] Int. Cl.² ........................................ C07D 251/32
[58] Field of Search ............................ 260/248 A

[56] References Cited
UNITED STATES PATENTS

| | | | |
|---|---|---|---|
| 3,325,493 | 6/1967 | Shimamura et al. | 260/248 |
| 3,878,208 | 4/1975 | Carlson et al. | 260/248 |

*Primary Examiner*—John M. Ford
*Attorney, Agent, or Firm*—Cushman, Darby & Cushman

[57] ABSTRACT

The process of the invention is directed to an improvement in purifying cyanuric acid which contains as a contaminant, an enclosed residue of a solvent used in the reaction mediums to produce cyanuric acid from urea, biuret or mixtures thereof. The process comprises suspending the impure cyanuric acid in an aqueous medium and stirring. As a result of the process, cyanuric acid is substantially freed from enclosed residues of contaminants solvents.

12 Claims, No Drawings

PROCESS FOR PURIFYING CYANURIC ACID

The invention is directed to purifying cyanuric acid which contains as a contaminant a residue of a polar solvent enclosed in the solid product.

BACKGROUND OF THE INVENTION

Cyanuric acid can be prepared by heating urea, biuret or mixtures thereof in the presence of a solvent. In the literature, a great number of different solvents, sometimes referred to as distributing agents, are described, many of which are polar and, water-soluble to varying degree. Examples of suitable distributing agents are sulphones, like dimethylsulphone, dipropylsulphone and sulpholane, chlorocresols, N-methylpyrrolidone, 5-methyl-2-oxazolidinone and methyl-substituted cyclohexanols, as well as the reaction products of these solvents with urea and biuret. Since cyanuric acid is only slightly soluble in those distributing agents, a suspension of the product cyanuric acid in the distributing agent is obtained when urea, biuret or mixtures thereof are heated in those distributing agents. The cyanuric acid can be separated therefrom.

It has been discovered that cyanuric acid prepared and isolated from the aforementioned reaction mixtures shows traces of the distributing agent used enclosed in the solid product, which are removed only with great difficulty. It is not possible, for instance, to remove these residues of the distributing agent by washing them out, unless such hugh amounts of washing liquid are used as to cause a large portion of the cyanuric acid to become dissolved, which, of course, is highly uneconomical. Yet, it is desirable for many applications that the cyanuric acid be freed from these residues of the distributing agent.

The invention relates to a process for purifying cyanuric acid which contains residues of a polar distributing agent enclosed in the solid cyanuric acid.

SUMMARY OF THE INVENTION

According to the invention cyanuric acid containing enclosed residues of a polar distributing agent which can be removed only with difficulty is purified by stirring up the contaminated cyanuric acid with an aqueous medium, whereupon the purified solid cyanuric acid is separated from the aqueous phase, Said "stirring up" is clearly distinct from the normal procedure of washing out, which requires little or no stirring and which does not result in cyanuric acid freed from enclosed residues of distributing agent. The stirring up is distinguished from recrystallization in that the cyanuric acid is suspended in accordance with the process of the invention and is not completely dissolved in the aqueous medium. In the stirring up treatment according to the invention, small amounts of aqueous medium are employed to remove the contaminant from the cyanuric acid and, hence, much less cyanuric acid is left behind in the mother liquor. In addition, the process of the invention does not require distinct and additional cooling or heating steps nor the concomittant for successive heating and cooling of the mixture. Further, the treatment according to the invention is much less time-consuming than is recrystallization.

DETAILED DESCRIPTION OF THE INVENTION

In accordance with the invention, cyanuric acid which contains as a contaminant an enclosed residue of a polar solvent is purified and freed of the polar solvent. The contaminated cyanuric acid is purified by stirring the contaminated cyanuric acid in an aqueous medium.

The stirring-up treatment according to the invention is preferably effected at temperatures ranging between 20° and 100° C. Lower temperatures, down to the solidification point, may be employed, but are unpractical. Higher temperatures, for instance, up to 200° C. may be employed, but do not offer any special advantages. At excessively high operating temperatures, the solubility of cyanuric acid is unpractically high, which may result in losses of some of the cyanuric acid. Moreover, hydrolysis of the cyanuric acid may occur at excessively high operating temperatures. The operating pressure is not critical and, therefore, is preferably atmospheric pressure. Higher and lower operating pressures, for instance, of between 0.2 and 10 atmospheres, may be applied, but do not offer any advantages as a rule.

Preferably, the cyanuric acid to aqueous medium mixing ratio is such that a 5–40 % by weight cyanuric acid suspension is obtained, more preferably a 15–30% by weight suspension.

As the aqueous medium, water alone may be employed. Also, mixtures of water and water-soluble, organic solvents that do not react with cyanuric acid under the treatment conditions may be used as the aqueous medium, said mixtures preferably containing at least 5% by weight, but preferably at least 25% by weight of water. The water-soluble organic solvents are preferably those which find application as distributing agents in the preparation of cyanuric acid by heating of urea and/or biuret and include dimethylsulphone, dipropylsulphone, o-chlorocresol, p-chlorocresol, N-methylpyrrolidone, N-cyclohexylpyrrolidone, 5-methyl-2-oxazolidinone, 2-methylcyclohexanol, 2,6-dimethylcyclohexanol, 2,4,6-trimethylcyclohexanol, sulpholane and methyl-substituted derivatives of sulpholane. Other suitable water-soluble solvents are other alcohols, ethers and esters or amides of carboxylic acids, with 1 to 12 carbon atoms, e.g. methanol, ethanol, propanol-2, diethylether, dimethylformamide or ethylacetate.

Preferably, the aqueous medium is a mixture of water and the distributing agent which is to be removed as a contaminant from the cyanuric acid is used. These mixtures contain up to 50% by weight, sometimes even up to 75% by weight, of the distributing agent, for effective removal of the distributing agent residues from the cyanuric acid. It is particularly surprising that it is possible to purify cyanuric acid containing 0.3% by weight of distributing agent as a contaminant by stirring up the contaminated cyanuric acid with a mixture of, for instance 50 % by weight of water and 50% by weight of the same distributing agent.

According to a preferred embodiment of the process according to the invention, the aqueous phase resulting from the purification of cyanuric acid has been separated off, recycled and used repeatedly for purification of fresh quantities of contaminated cyanuric acid. Recycling of the aqueous phase resulting from purification of cyanuric acid may be undertaken until the aqueous phase contains 10 – 50% by weight of the distributing agent. In a continuous process (1) a quantity of aqueous phase is continuously discharged from the system so that the amount of distributing agent therein corresponds with the amount of distributing agent removed from the cyanuric acid, and (2) water is added to the aqueous phase, so that the total volume of the aqueous phase remains constant. In this way, it is possible for the distributing agent to be recovered from the discharged aqueous phase in an economically justified manner.

The stirring-up procedure of the invention is preferably undertaken for a period of at least 5 minutes, in order to obtain a substantial removal of the enclosed contaminants. Usually, residence times is in excess of 3 hours serve no purpose. Preferably, residence times in the stirring-up step range between 10 and 30 minutes, with virtually complete removal of distributing agent residues.

The purified, solid cyanuric acid may be separated from the aqueous phase by any known technique for the separation of a solid and a liquid, for instance, by filtering off, centrifuging, settlement and pouring off, and the like.

The distributing agent to be removed may be any distributing agent which, at the stirring-up temperatures, dissolves in water at least to some degree, e.g., at a concentration of at least 0.1% by weight. Examples are dialkylsulphones or cyclic sulphones with 2 to 12 carbon atoms, halogen-substituted cresols and phenols; further, N-alkylpyrrolidones, N-substituted urethanes and cyclic urethanes in which the substituents are hydrocarbon groups of 1 to 6 carbon atoms; polyether alcohols; cyclic polyethers and cyclohexanol or substituted cyclohexanols substituted by one or more alkyl, cycloalkyl or aryl groups of 1 to 6 carbon atoms. Preferably, the terminology "hydrocarbon groups" refers to phenyl-, alkyl-, or cycloalkyl-groups. In the preparation of cyanuric acid by heating urea and/or biuret, the aforementioned distributing agents result in the advantage that urea and biuret are rather soluble in them, while cyanuric acid is not particularly soluble; as a result, separation of the cyanuric acid from the reaction mixture is relatively simple. Specific examples of the distributing agents are dimethylsulphone, dipropylsulphone, o- and p-chlorocresol, N-methylpyrrolidone, N-cyclohexylpyrrolidone, 5-methyl-2-oxazolidinone, 2-methyl-cyclohexanol, 2,6-dimethyl-cyclohexanol, 2,4,6-trimethylcyclohexanol, and particularly, sulpholane and its methyl-substituted derivatives.

The content of enclosed distributing agent residue contaminating the cyanuric acid which residue is difficult to remove by conventional methods is for example from 0.05 to 0.5% by weight, particularly from 0.2 to 0.5% by weight. In addition, the cyanuric acid to be treated may still contain easily removable, adhering distributing agent. After the purifying treatment according to the invention the content of distributing agent residues is reduced to less than 0.05% by weight. The cyanuric acid purified according to the invention is suitable for many applications, for instance, as starting material in the preparation of chlorinated derivatives, tris(hydroxyethyl)isocyanurate, triallylisocyanurate and the like.

EXAMPLE I

Crude cyanuric acid was obtained by heating urea in sulpholane as distributing agent, followed by separation of the solid. After the washing out with benzene for removal of adhering distributing agent, the cyanuric acid obtained contained 0.41% by weight of sulpholane (calculated from the sulphur content). For 15 minutes, at a temperature of 80° C. and under atmospheric pressure, one portion was stirred up with a three-fold amount by weight of water. Next, the solid was filtered off, dried and analyzed for sulphur. The presence of sulphur could no longer be demonstrated in the cyanuric acid obtained. The detection limit amounted to 0.01% by weight.

EXAMPLE II

A second, equally large portion of the same impure cyanuric acid starting material was stirred up with the filtrate of Example I for 15 minutes, under the same conditions as those of Example I. Again, the presence of sulphur could no longer be demonstrated in the cyanuric acid obtained.

EXAMPLE III

The procedure according to Example I was followed, except for the temperature, which now amounted to 25° C. The cyanuric acid obtained contained less than 0.01% by weight of sulphur.

EXAMPLE IV

The procedure according to Example I was followed. As aqueous medium for stirring up, however, no water, but a solution of 55.5% by weight of sulpholane in water was applied. Further, the stirring-up lasted 60 instead of 15 minutes. The presence of sulphur could not longer be demonstrated in the cyanuric acid obtained.

Comparative Experiment A

Crude cyanuric acid was obtained by heating urea in sulpholane as distributing agent, followed by separation of the solid. After the washing out with benzene for removal of adhering distributing agent, the cyanuric acid obtained contained 0.26% by weight of sulpholane (0.07% by weight of sulphur). One portion was boiled for 3 hours, with stirring and with reflux of the condensed vapour, at atmospheric pressure with the tenfold amount by weight of benzene. Next, the solid was filtered off and dried. It appeared still to contain 0.06% by weight of sulphur. This vigorous treatment, therefore, had produced practically no result.

Comparative Experiment B-K

The procedure according to Example I was followed, on the understanding that the operating temperature amounted to 80° C. or, if it was lower, the boiling temperature at 1 atmosphere, whilst the stirring-up time amounted to 1 hour. Instead of the aqueous medium various organic solvents having a water content of less than 0.2% by weight were used, with the exception of the methanol, which contained 0.7% by weight of water. The initial sulpholane concentration in the cyanuric acid invariably amounted to 0.30% by weight. The results are given in the following table.

TABLE

| Experiment | Solvent | % By Weight Of Sulpholane In Cyanuric Acid Treated |
|---|---|---|
| B | Dimethylformamide | 0.30 |
| C | N-methylpyrrolidone | 0.26 |
| D | Dioxane | 0.23 |
| E | Methanol | 0.34 |
| F | Trichloroethylene | 0.30 |
| G | 1-hydroxy-2-methoxy-ethane ('monomethyl-cellosolve') | 0.26 |
| H | Ethylacetate | 0.30 |

TABLE -continued

| Experiment | Solvent | % By Weight Of Sulpholane In Cyanuric Acid Treated |
|---|---|---|
| K | Diethylether | 0.30 |

Comparative Experiment L

The crude cyanuric acid with a sulphur content of 0.11% by weight used in Example I was washed out 5 times, each time with an amount by weight of water which was equal to the amount of cyanuric acid. After the drying, the cyanuric acid contained 0.09% by weight of sulphur. This shows that the washing out treatment does not produce any substantial result.

EXAMPLE V

The procedure according to Comparative Experiment K was followed, but diethylether was used, however, which was saturated with water at 20° C. The water content amounted to approximately 1.2% by weight. The cyanuric acid treated still contained 0.15% by weight of sulpholane.

What is claimed is:

1. A process for purifying cyanuric acid containing enclosed residues of a polar distributing agent as contaminants comprising mixing the impure cyanuric acid with an aqueous medium to form suspension of cyanuric acid in the medium and stirring said suspension for a period of time of at least 5 minutes; and separating solid cyanuric acid by conventional separation techniques.

2. Process according to claim 1, wherein the cyanuric acid aqueous medium suspension is 5–40% by weight cyanuric acid suspension.

3. Process according to claim 2, wherein a 15-30% by weight cyanuric acid suspension is employed.

4. Process according to claim 2, wherein the aqueous medium is water.

5. Process according to claim 2, wherein the temperature of the suspension of cyanuric acid ranges between 20° – 100° C.

6. Process according to claim 5, wherein said impure cyanuric acid is produced by heating urea, biuret or mixtures thereof, in a distributing agent to produce cyanuric acid and by separating cyanuric acid as a product, said product containing the distributing agent as a contaminant.

7. Process according to claim 2, wherein the aqueous medium is water or an aqueous solution of a solvent which is identical to the contaminant distributing agent residues, wherein said solvent comprises 5 to 75% by weight of the aqueous solution.

8. Process according to claim 7, wherein said solvent is dimethylsulphone, dipropylsulphone, o-chlorocresol, p-chlorocresol, N-methylpyrrolidone, N-cyclohexylpyrrolidone, 5-methyl-2-oxazolidinone, 2-methylcyclohexanol, 2,6-dimethylcyclohexanol, 2,4,6-trimethylcyclohexanol, sulpholane, or methyl-substituted derivatives of sulpholane.

9. Process according to claim 8, wherein said period of time ranges between 10 - 30 minutes.

10. Process according to claim 9, wherein said solvent is sulpholane.

11. Process according to claim 7, wherein said aqueous solution contains 10 – 50% by weight of the distributing agent, and wherein the aqueous phase, resulting from said step of separation, is discharged and recycled to said step of mixing and stirring.

12. Process according to claim 1, characterized in that the distributing agent to be removed from the cyanuric acid has been chosen from the dialkylsulphones or cyclic sulphones with 2 to 12 carbon atoms; halogen-substituted cresols or phenols; N-alkylpyrrolidones, N-substituted urethanes and cyclic urethanes in which the substituents are hydrocarbon groups of 1 to 6 carbon atoms; polyetheralcohols; cyclic polyethers; cyclohexanol, and substituted cyclohexanols with one or more hydrocarbon groups of 1 to 6 carbon atoms each for substituents.

* * * * *